US006527758B2

(12) United States Patent
Ko

(10) Patent No.: US 6,527,758 B2
(45) Date of Patent: Mar. 4, 2003

(54) VIAL DOCKING STATION FOR SLIDING RECONSTITUTION WITH DILUENT CONTAINER

(76) Inventor: Kam Ko, 92 Morrison Crescent, Unionville, Ontario (CA), L3R 9K8

( * ) Notice: Subject to any disclaimer, the term of this patent is extended or adjusted under 35 U.S.C. 154(b) by 0 days.

(21) Appl. No.: 09/878,543

(22) Filed: Jun. 11, 2001

(65) Prior Publication Data

US 2002/0188273 A1 Dec. 12, 2002

(51) Int. Cl.$^{7}$ .......................... A61B 19/00; A61B 17/43

(52) U.S. Cl. ....................... 604/403; 604/410; 604/411; 604/412; 604/414; 604/415; 604/416; 604/905

(58) Field of Search ................................ 604/403, 410, 604/411, 412, 414, 415, 416, 83, 88, 905; 222/81; 137/614.04; 206/221, 265

(56) References Cited

U.S. PATENT DOCUMENTS

| | | | | | |
|---|---|---|---|---|---|
| 1,657,782 | A | | 1/1928 | Berg | |
| 3,245,586 | A | | 4/1966 | Haggitt | 222/88 |
| RE30,610 | E | | 5/1981 | Gacki et al. | 366/153 |
| 4,936,841 | A | | 6/1990 | Aoki et al. | 604/413 |
| 5,037,390 | A | | 8/1991 | Raines et al. | 604/83 |
| 5,190,525 | A | * | 3/1993 | Oswald et al. | 604/83 |
| 5,329,976 | A | * | 7/1994 | Haber et al. | 141/18 |
| 5,364,386 | A | | 11/1994 | Fukuoka et al. | 604/411 |
| 5,372,593 | A | * | 12/1994 | Boehringer et al. | 604/317 |
| 5,409,141 | A | | 4/1995 | Kikuchi et al. | 222/81 |
| 5,478,337 | A | | 12/1995 | Okamoto et al. | 604/413 |
| 5,596,193 | A | * | 1/1997 | Chutjian et al. | 250/281 |
| 5,782,382 | A | * | 7/1998 | Van Marcke | 222/105 |
| 5,826,713 | A | | 10/1998 | Sunago et al. | 206/222 |
| 6,063,068 | A | * | 5/2000 | Fowles et al. | 604/411 |
| 6,065,649 | A | | 5/2000 | Scoggins | 222/181.2 |
| 6,070,761 | A | | 6/2000 | Bloom et al. | 222/81 |
| 6,113,583 | A | | 9/2000 | Fowles et al. | 604/403 |

* cited by examiner

*Primary Examiner*—William C. Doerrler
*Assistant Examiner*—Filip Zec
(74) *Attorney, Agent, or Firm*—Mark Kusner; Michael A. Jaffe

(57) ABSTRACT

A vial docking station for simultaneously sliding the spouts of a plurality of liquid medicament vials into an engaged position with matching receptacles of a like plurality of liquid reconstitution diluent bags.

10 Claims, 10 Drawing Sheets

22
24
10
16
14
30
28

VIAL DOCKING STATION FOR SLIDING RECONSTITUTION WITH DILUENT CONTAINER

TECHNICAL FIELD

The invention relates to a vial docking station for simultaneously sliding the spouts of a plurality of liquid medicament vials into an engaged position with matching receptacles of a like plurality of liquid reconstitution diluent bags.

BACKGROUND OF THE ART

In hospital pharmacies, a common activity is to prepare several intravenous delivery bags with saline solutions for example to be mixed with various liquid medicaments to the specification of doctors. Often, the liquid medicines are provided in vials or glass bottles with a rubber sheet diaphragm across the spout of the bottle sealed with a metal rim and removable seal. The liquid medicines can be accessed by hypodermic needle for example, piercing through the rubber diaphragm and withdrawing liquid medicine into a hypodermic needle. Also commonly in hospitals, the vials are provided in measured doses by the drug manufacturer and the hospital pharmacy prepares intravenous solutions by engaging the spouts of the vials with matching receptacles on the sealed sterile diluent bags. The receptacles include sliding or telescoping means to engage a piercing needle on the receptacle and release the medicine from the vials into the saline solution in the diluent bag by permitting air to pass one way into the vial and thereby releasing the liquid through the needle.

Manually engaging the vials with receptacles of diluent bags involves many risks including physical injury or biological contamination from sharp needles, contamination of adjacent atmosphere with powerful or toxic medicines, and exposure of pharmacy workers to long term low concentrations of drugs. In order to address these risks, the prior art includes various mechanical devices to ensure safe engagement of vials with the receptacles and includes mechanical devices that can be positioned under exhaust hooks to avoid contamination.

U.S. Pat. No. 5,037,390 to Raines et al. shows a method of preparing diluent solution bags from a number of different vials of medicines of different sizes. The fluid medicament from the vials is conducted through a perforated needle in a one way valve into a manifold, which conducts the mixture of medicines to a diluent bag for delivery to the patient.

U.S. Pat. No. 6,070,761 to Bloom et al. shows a complex automatic system for mixing medicines for multiple vials that are delivered through needles into a plastic cassette with various channels and vials are mixing and delivering the medicament to an automatic delivery system.

Simple manual mechanisms for engaging a diluent bag with piercing needle and vials minimizing the risk of injury and exposure are shown in several patents such as U.S. Pat. No. 5,826,713 to Sunago et al., U.S. Pat. No. 5,478,337 to Okamoto et al. and U.S. Pat. No. 5,364,386 to Fukuoka et al. Apart from the examples mentioned above, it is considered well known to those in the relevant art that various devices are available for connecting vials containing medicaments with flexible diluent bags containing saline solutions.

A significant disadvantage of the prior art devices is the high cost and mechanical complexities. Due to these disadvantages, many hospital pharmacies rely on the physical labour of pharmacists to connect vials with receptacles individually. This method leads to fatigue and mistakes, personal injury and exposure to biological hazards as well as concentrated medicines which impose unacceptable risks to workers in hospital pharmacies as a result.

An unrecognised, but major cause of illness and some times death is human error in preparing medicines, which are delivered in the wrong concentration or to the wrong patient.

It is an object of the present invention to provide a simple low cost reliable tool for engaging vials of various sizes to diluent bags thus avoiding human contact and physical exertion as much as possible.

It is a further object of the invention to provide a mechanical system wherein vials of different sizes can be prepared in a ready position and double-checked before mixing for example with bar code readers in an optical checking system.

It is a further object of the invention to provide optional manually operated vial docking station and pneumatic or hydraulically operated version without significant modification to the mechanism.

Further advantages of the invention will be apparent from the following detailed description and accompanying drawings.

DISCLOSURE OF THE INVENTION

The invention provides a vial docking station for simultaneously sliding the spouts of a plurality of liquid medicament vials into an engaged position with matching receptacles of a like plurality of liquid reconstitution diluent bags. The vial docking station has a support frame that can be mounted to a wall or within an exhaust hood to reduce the risk of exposure.

The frame has a stationary bag mounting block with a series of spaced apart receptacle mounts. The mounts are C-shaped for suspending the diluent bags from their flexible inlet tube and receptacles below the mounting block. For different sizes or designs of receptacles, the mounts can include replaceable inserts or ferrules of different designs.

A header block is slidably mounted to the frame and has an equal number of plungers that are used to hold vials in an upturned position and to force the vial spout into sliding engagement with the receptacle. Each plunger is spring loaded or biased to firmly hold and guide the base of an associated vial in a ready position. In this position the vial is upturned to flow out under gravity when the seal diaphragm is pierced with the needle of the receptacle. The vial spout is aligned with the receptacle ready to be forced into sliding engagement with the plungers. Each plunger is manually individually operable between the ready position and a retracted position wherein the vial base is manually lifted against the force of gravity and spring load to be disengaged from the plunger.

Plunger clamps are disposed on the header block, for releasably clamping each plunger to move with the header block. A manually operated or mechanically operated actuation mechanism is mounted to the frame and engages the plunger clamps and the moveable header block for moving the header block progressively from the ready position forward to the engaged position, and rearward to a withdrawn position and for actuating the plunger clamps during movement between the ready position and the withdrawn position.

The plungers have a head with a conical self-centering vial base mating socket and a rod slidably mounted to the header block. The plunger head is spring loaded toward the bag mounting block to hold the vials ready in an upturned position above the bag receptacles.

The plunger clamp has a lock lever pivotally mounted to the header block for rotation about an axis transverse to the plunger rod. The rod extends through an aperture through the lock lever and the lock lever can move between a free sliding position and a clamped position wherein lock lever is disposed relative to the plunger rod with peripheral edges of the aperture gripping an outer surface of the rod. The offset aperture therefore binds or grips the cylindrical rod.

Further advantages of the invention will be apparent from the following detailed description and accompanying drawings.

DESCRIPTION OF THE DRAWINGS

In order that the invention may be readily understood, two embodiments of the invention are illustrated by way of example in the accompanying drawings.

FIG. 16 and 17 show detailed sectional views of the cam shaft with cam lobe that engages and disengages the lock lever in FIG. 16 showing the lock lever disengaged from the plunger rod, whereas FIG. 17 shows the binding between the aperture in the lock lever and the cylindrical plunger rod.

Further details of the invention and its advantages will be apparent from the detailed description included below.

DETAILED DESCRIPTION OF PREFERRED EMBODIMENTS

Figure 1:
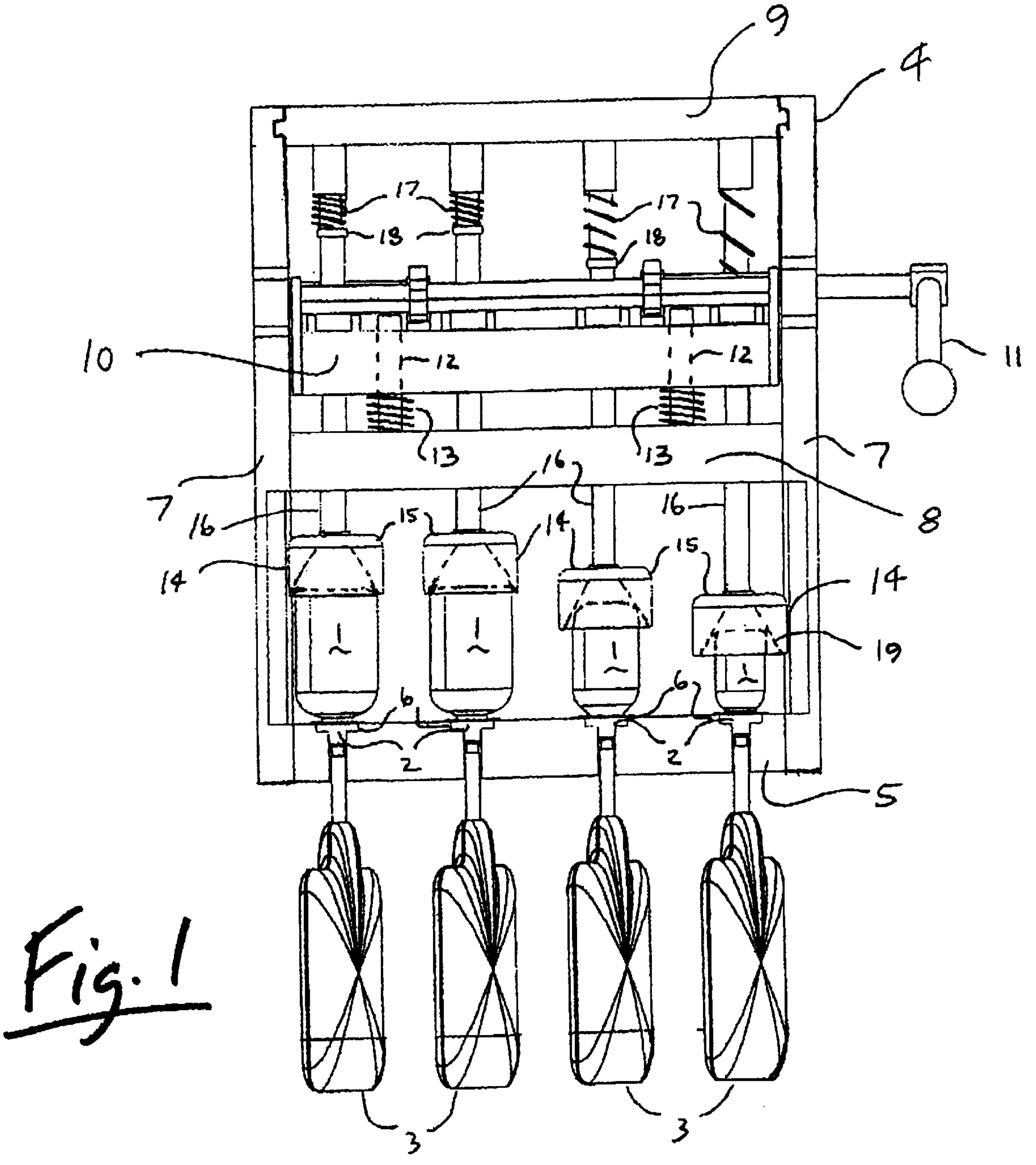
FIG. 1 is a front elevation view of a manually operated embodiment of the invention showing a rectangular frame with bag mounting block suspending four diluent bags by their receptacles and including four vials in an inverted or upturned position aligned with the receptacles, the vials being of different sizes adapted with the spring loaded plungers.
Figure 2:
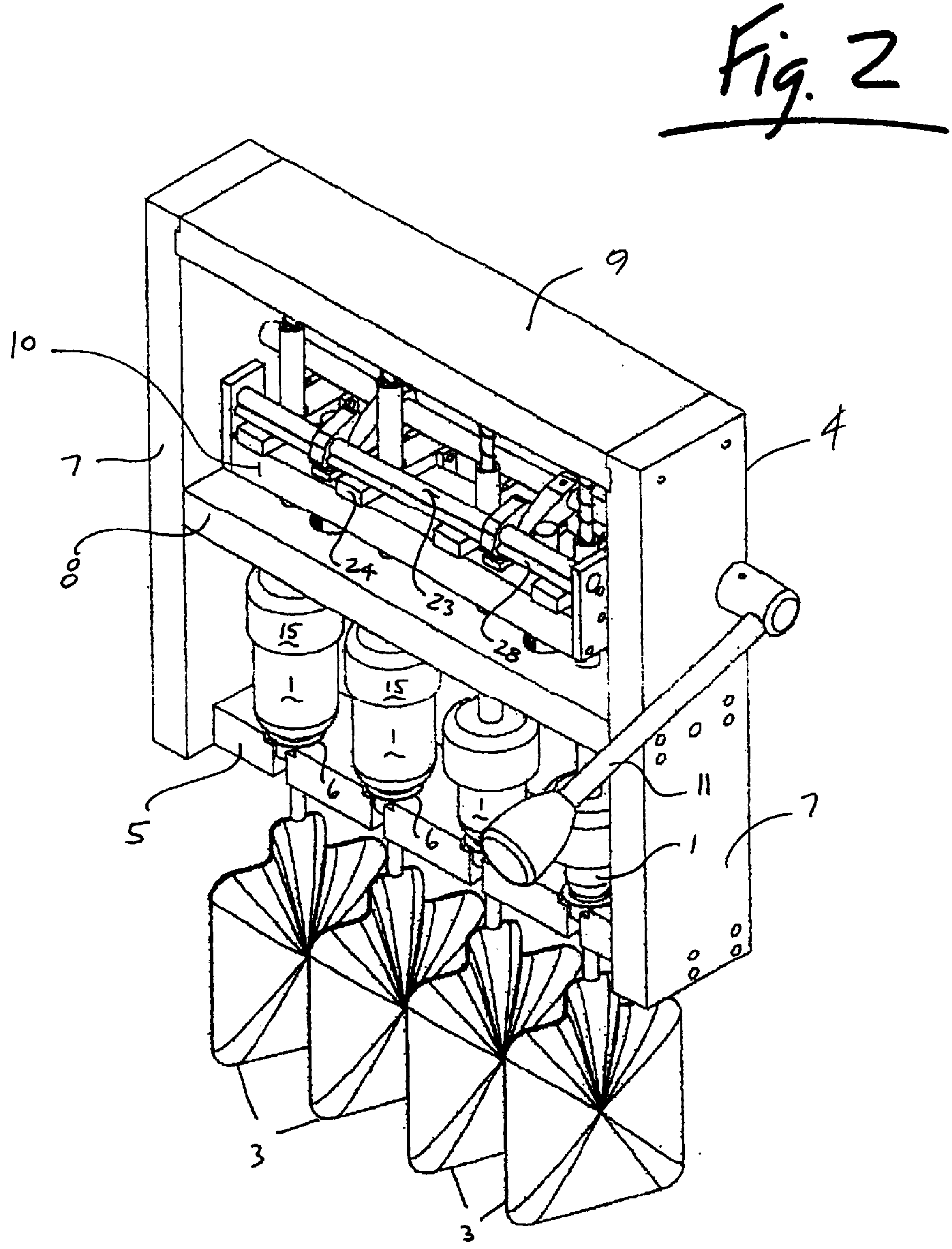
FIG. 2 is a perspective view of the manual embodiment shown in FIG. 1.
Figure 3:
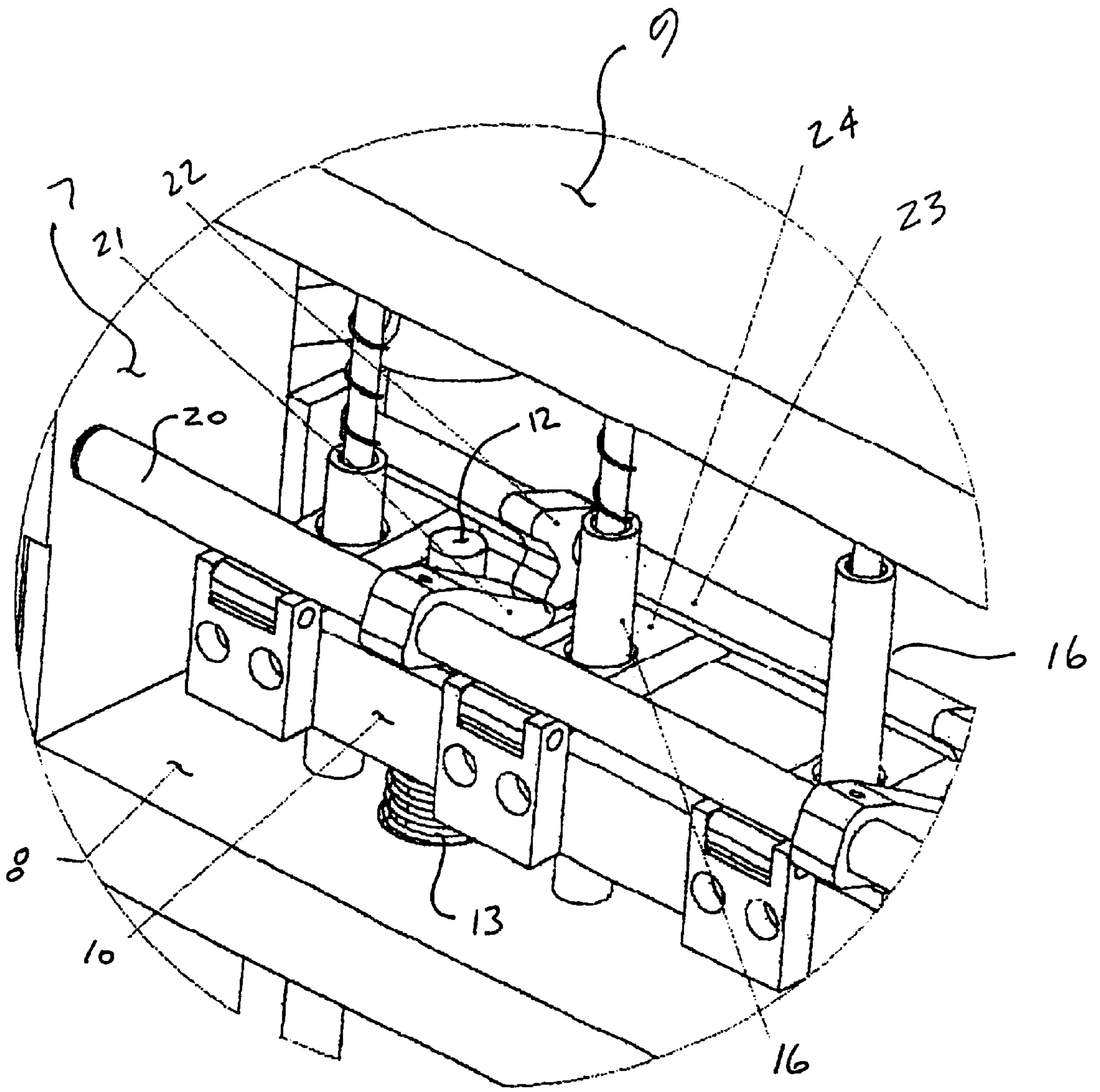
FIG. 3 is a detailed view of the manual embodiment with the crank shaft, cam shaft and lock levers positioned on the movable header block spring loaded upwardly from the stationary bag mounting block.
Figure 5:
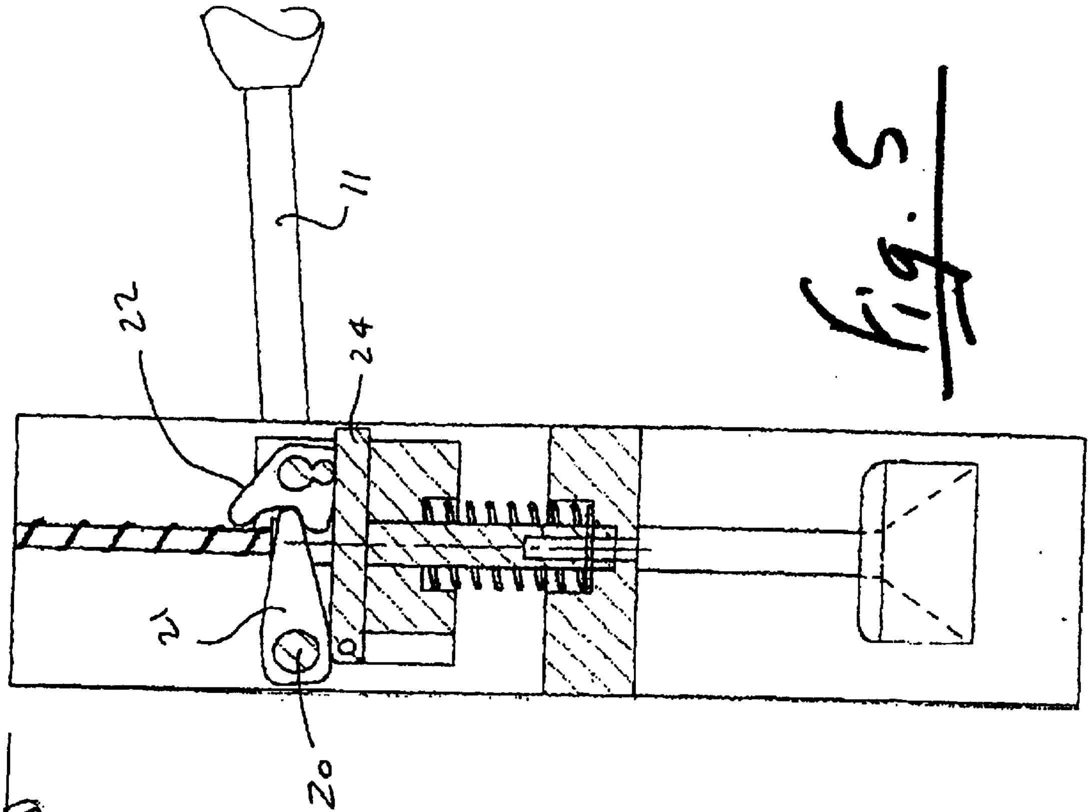
FIGS. 4, 5, 6, and 7 show the progressive downward motion of the crank arm of the manual embodiment which is manually rotated clockwise to simultaneously force the movable headed block downwardly and clamp the plungers to move with the header block by releasing the lock levers to bind with the cylindrical rods of the plunger.
Figure 4:
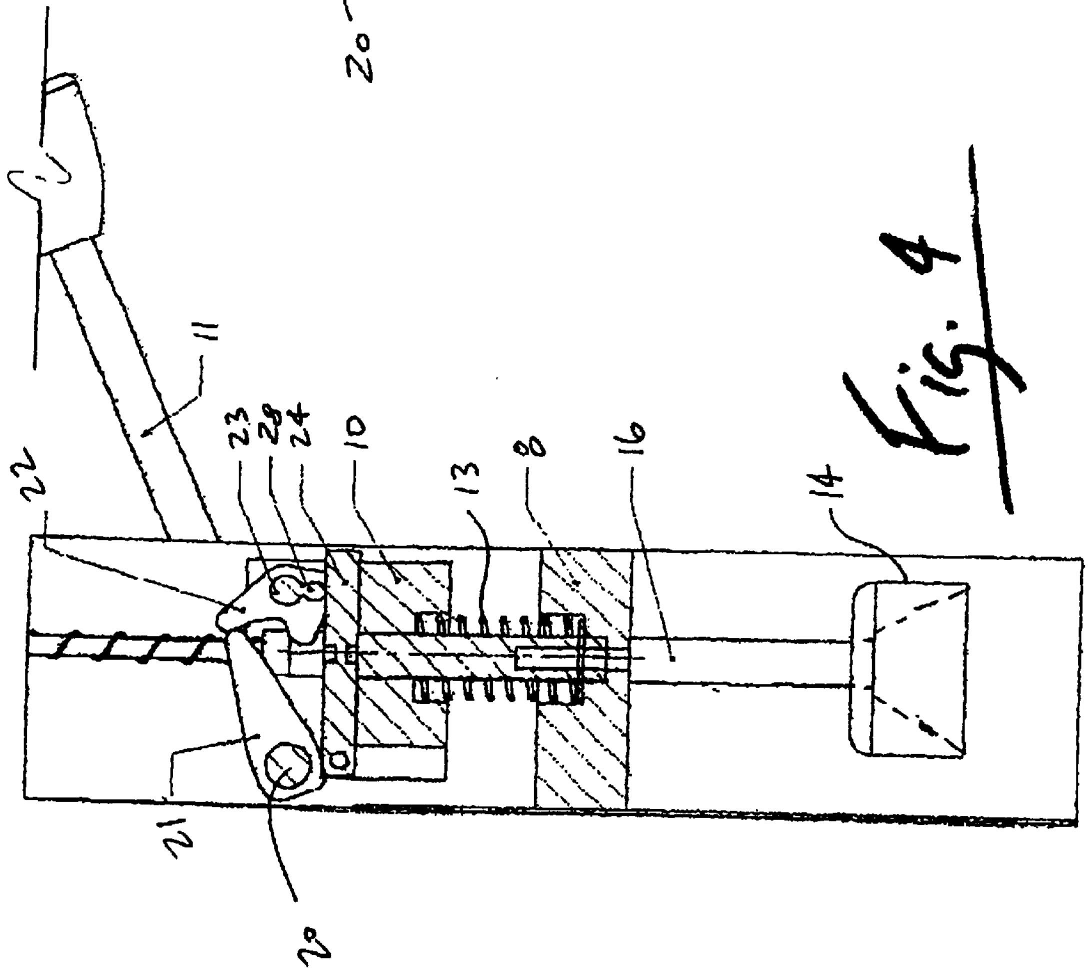

With reference to FIGS. 1 and 2, the invention provides a manually operated vial docking station that accommodates vials 1 of different common sizes and simultaneously slides the spout of the inverted or upturned vials 1 into an engaged position with matching receptacles 2 of a spaced apart series of diluent bags 3.

The vial docking station includes in the embodiment illustrated a rectangular frame 4 for hanging on a wall in a vertical position. It will be understood that different embodiments can be provided for table top use or in a is horizontal position with equal advantage. The frame 4 includes a horizontal bag mounting block 5 with a spaced apart series of receptacle mounts 6. The embodiment illustrated shows the bag mounting block 5 fixed in position to side walls 7. The stationary portions of the frame also include middle beam 8 and top beam 9.

A slidable header block 10 is manually operated with crank arm 11 in a manner, which will be described in detail below. The header block 10 slides on vertical pins 12 and is spring loaded to an upward position against middle beam 8 with springs 13.

The header block 10 also includes plungers 14 that are clamped and unclamped to move simultaneously up and down with the header block 10 thereby exerting force on the bottom of the vials 1 sufficient to slidably engage the spout of the vials in the receptacles 2.

The plungers 14 include a head 15 and a rod 16. The rods are guided but otherwise free to slide through middle beam 8 and slide through header block 10 when unclamped. Clamps on the header lock 10 that secure the rods 16 to the header block 10 are actuated by the manual motion of the crank arm 11 once the vials are manually placed in position shown in FIGS. 1 and 2. A spring 17 engaging a collar 18 on the slidable rods 16 together with the gravitational force of the weight of the plunger 14 hold the vials 1 in a ready position. The operator grasps the plunger head 15 and lifts upward to a withdrawn position against the force of the spring 17 to insert and remove the vials 1. In the embodiment shown the plunger heads 15 have a conical self centering socket 19 for locating and holding the base of any size of vial 1.

FIGS. 4, 5, 6, and 7 show the manual embodiment of the invention in a sectional view through middle beam 8 and movable header block 10. The header block 10 is mounted to middle beam 8 of the frame on pins 12 with spring 13 to slide up and down during manual operation of the crank arm 11 in a clockwise direction progressing from FIG. 4 through FIG. 7.

Figure 7:
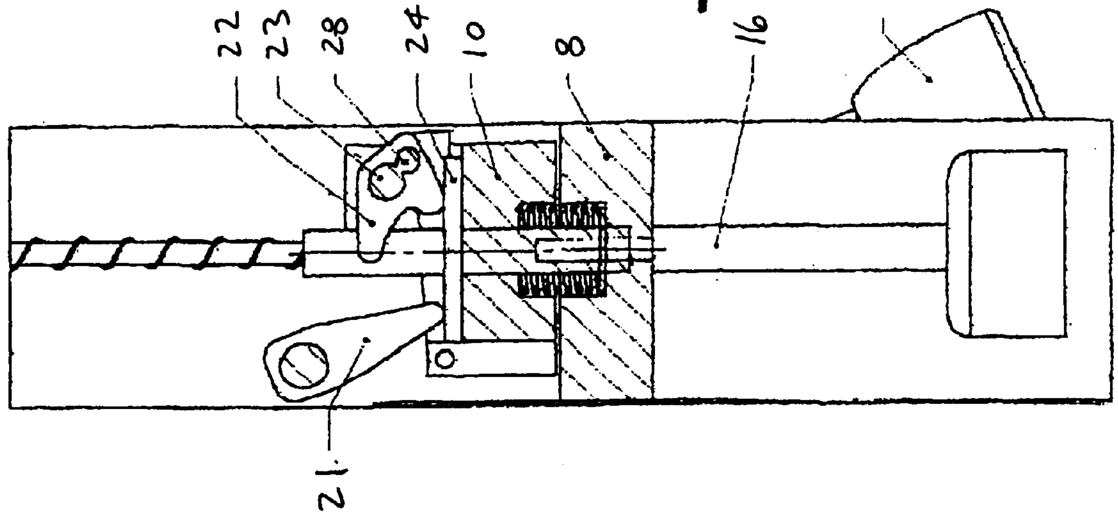

Rotation of the crank arm 11 rotates crank shaft 20. and lever arm 21, which engages cam follower 22 thereby rotating cam shaft 23. Rotation of the cam shaft 23 with cam lobe 28 releases spring loaded lock lever 24 to the position shown in FIGS. 6 and 7 binding on the rod 16 extending through lock lever 24. Further rotation of the lever arm 21 engages a top surface of the header block 10 pushing the plungers 14 downwardly to the engaged position as shown in FIG. 7.

To recap therefore the header block 10 mounts to the frame with series of plungers 14, each of which is biased to engage the base of an associated vial 1 in a ready position as shown in FIGS. 1 and 2.

Each plunger 14 is manually, individually operable between the ready position shown in FIG. 1 and a retracted position for disengaging the vial base from the plunger 14.

Figure 9:
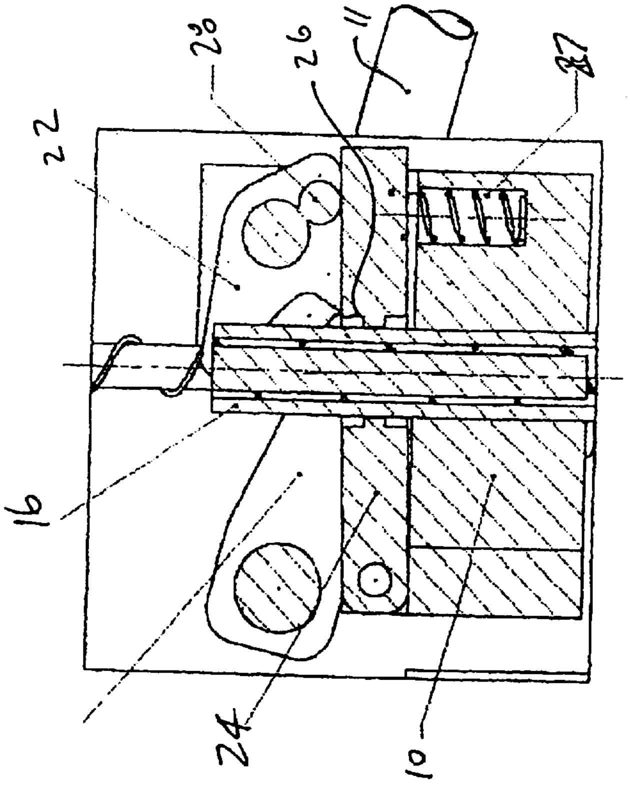
FIGS. 8 and 9 show detailed view of the lock lever of the manual embodiment spring loaded to an upward position and pivoted to allow the plunger rod to slide freely (in FIG. 8) and to bind the slide rod (shown in FIG. 9).
Figure 8:
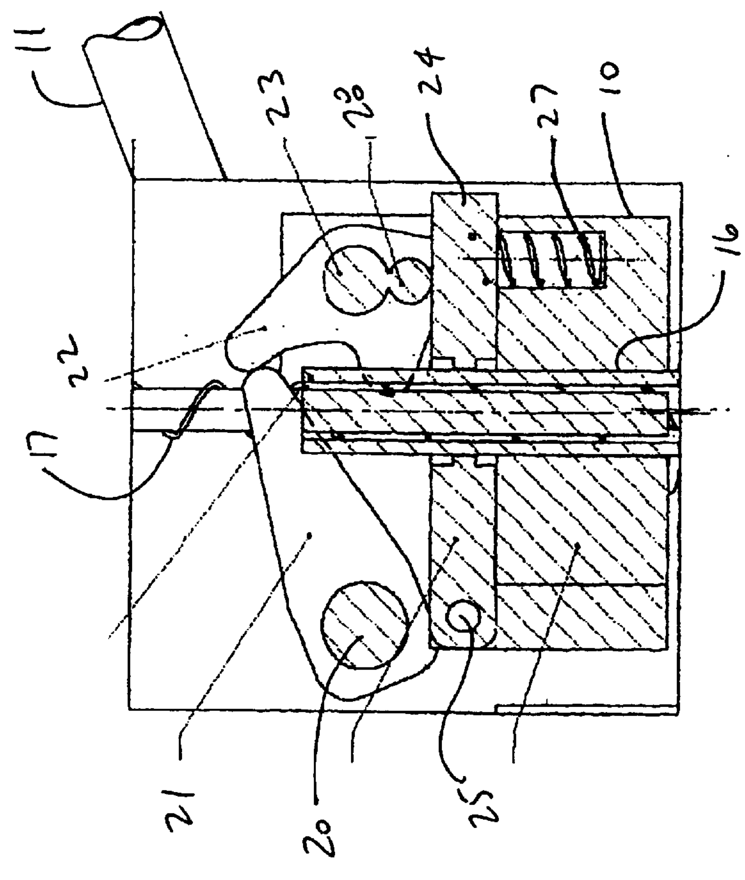

The plunger clamping position is illustrated in FIGS. 8 and 9 in detail. Plunger rods 16 engage through the movable header block 10 and are spring loaded to a downward position with springs 17. FIGS. 8 and 9 show the details of plungers clamps disposed. on the header block 10 to releasably clamp each plunger rod 16 and inhibit relative motion between the plunger 14 and the header block 10. The manual actuation mechanism comprising crank arm 11, crank shaft 20 and lever arm 21 as described above serve to engage the plunger clamps, the header block 10 or the bag mounting block 5 and move the header block 10 relative to the bag mounting block 5 from the ready position shown in FIG. 1 to the engaged position shown in FIG. 7 and rearwardly withdraw the header block 10 under the force of lift springs 13 automatically disengaging the plunger clamps.

As seen in FIGS. 8 and 9, the plunger clamps comprise a lock lever 24, which is pivotally mounted on pin 25 to rotate about an axis transverse to the plunger rod 16. The rod 16 extends through an aperture 26 extending through the lock lever 24. The lock lever 24 moves between the free sliding position shown in FIG. 24 and clamped position shown in FIG. 9. In the clamped position, the lock lever 24 is disposed relatively to the plunger rod 16 such as peripheral edges of the aperture 26 grip the outer cylindrical surface of the rod 16. The lock lever 24 is spring loaded to the upward position of FIG. 9 by spring 27. Since the aperture 26 in the sliding free position shown in FIG. 8 closely matches the outer cylindrical surface of the rod 16, only a slight offset motion (as illustrated in FIG. 9) is required in order to tightly bind the rod 16 in the aperture 26 and prevent movement relative to the header block 10. Rotation of the cam shaft 24 mounted to the header block 10 causes the cam lobe 28 to rotate (as shown between FIG. 8 and FIG. 9) in a counter clockwise motion thereby freeing the spring 27 to pivot the lock lever 24 about pin 25.

As best seen in the progression shown in FIGS. 4, 5, 6, and 7, the cam shaft 23 includes a cam follower 22 for rotating the cam shaft 23 as the header block 10 progresses between the ready position, a fully engaged position and a withdrawn position. In the withdrawn position, the vials 1 can be removed by raising the plunger 14 manually and lifting the empty vial from engagement with the receptacle 2. At this point, the bag 3 with sealing solution and mixed medicament can be delivered to patient care providers.

Figure 6:
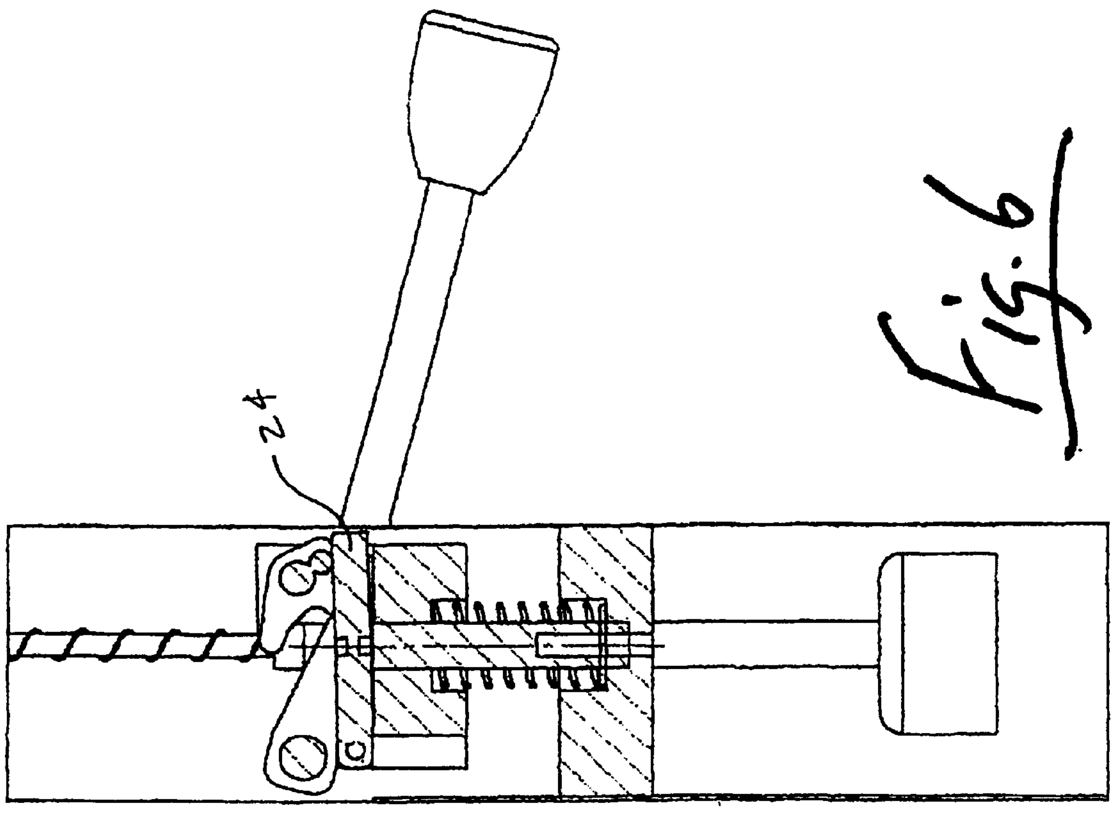

As seen in the progression between FIGS. 4, 5, 6, and 7, manual rotation of the crank shaft 20 with crank arm 11 rotates lever arm 21, which serves two functions. Firstly, interaction with cam follower 22 and lever arm 21 serves to rotate cam shaft 23 thereby releasing cam lobe 28 from engagement with lock lever 24. As shown in FIGS. 6 and 7, releasing lock lever 24 results in binding of the plunger rods 16 with the lock lever 24 as best seen in FIGS. 8 and 9. Further, manual rotation of the lever arm 21 as shown in FIGS. 6 and 7 pushes on the top surface of the header block 10 and brings the header block 10 with attached plungers downward against the force of spring 13 compressed between the header block 10 and stationary middle block 8.

Figure 10:
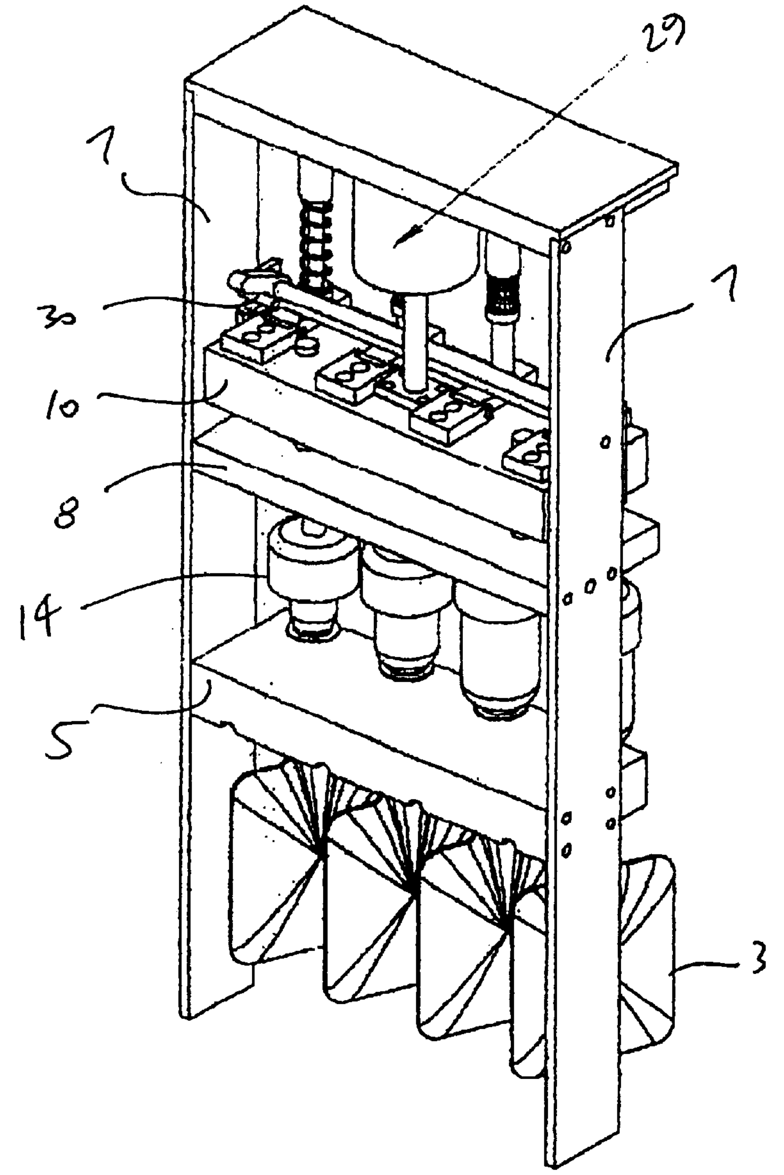
FIG. 10 shows a pneumatically or hydraulically actuated embodiment of the invention (similar to the view of the manual embodiment of FIG. 2 but shown from the rear rather than front view) with a single central actuating cylinder engaging the movable header block

FIGS. 10 through 17 disclose a second embodiment of is the invention that is not manually operated but rather is operated primarily through use of a pneumatic or hydraulic cylinder 29. As shown in FIG. 10, the cylinder actuates motion of the header block 10 sliding it vertically with respect to the stationary middle block 8 in a manner similar to that described above in respect of the manually operated embodiment.

In the mechanically operated embodiment, the mounting of the bags 3 in the bag mounting block 5 and the motion of the plungers 14 is identical to that described above. However, in the mechanically operated version there is no crank shaft 20, lever arm 21 or crank arms 11. The functions performed by these manually operated elements to rotate the cam shaft 23 and move the header block 10 are performed as follows.

Figure 16:
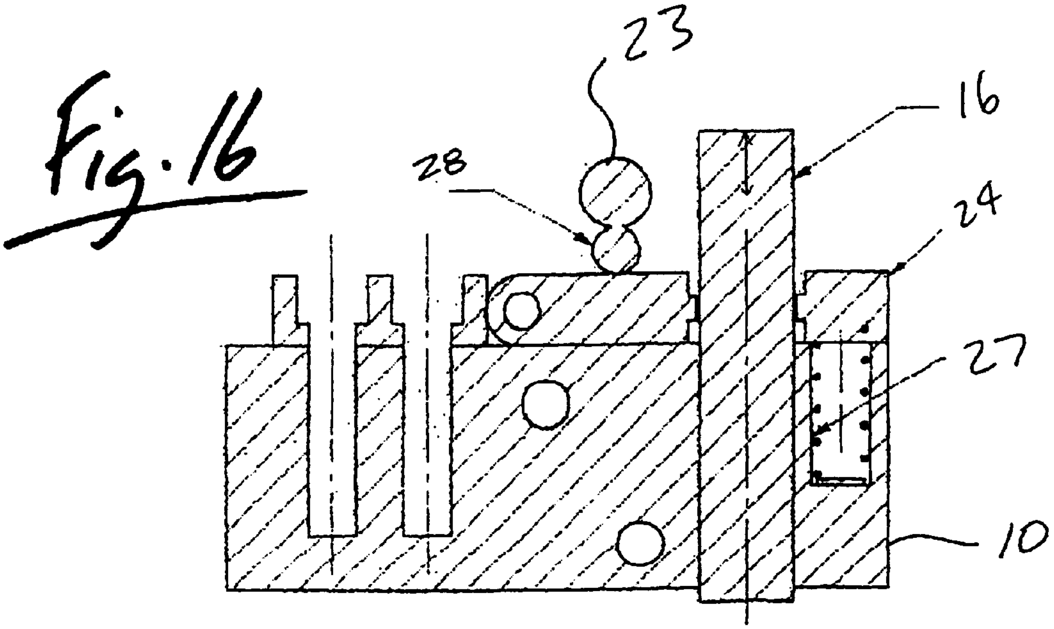
Figure 17:
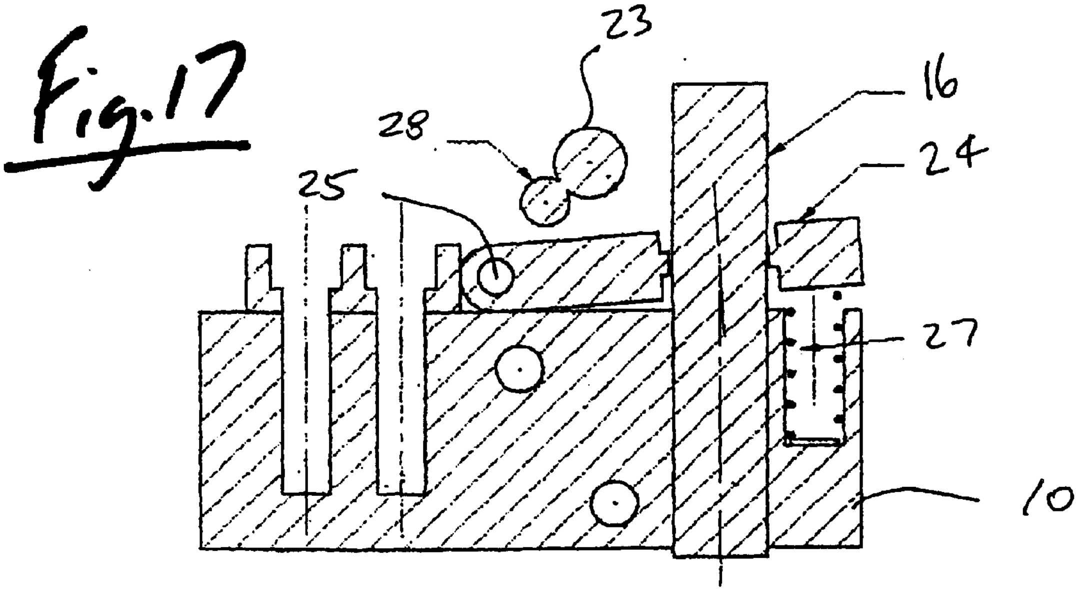
Figure 1:
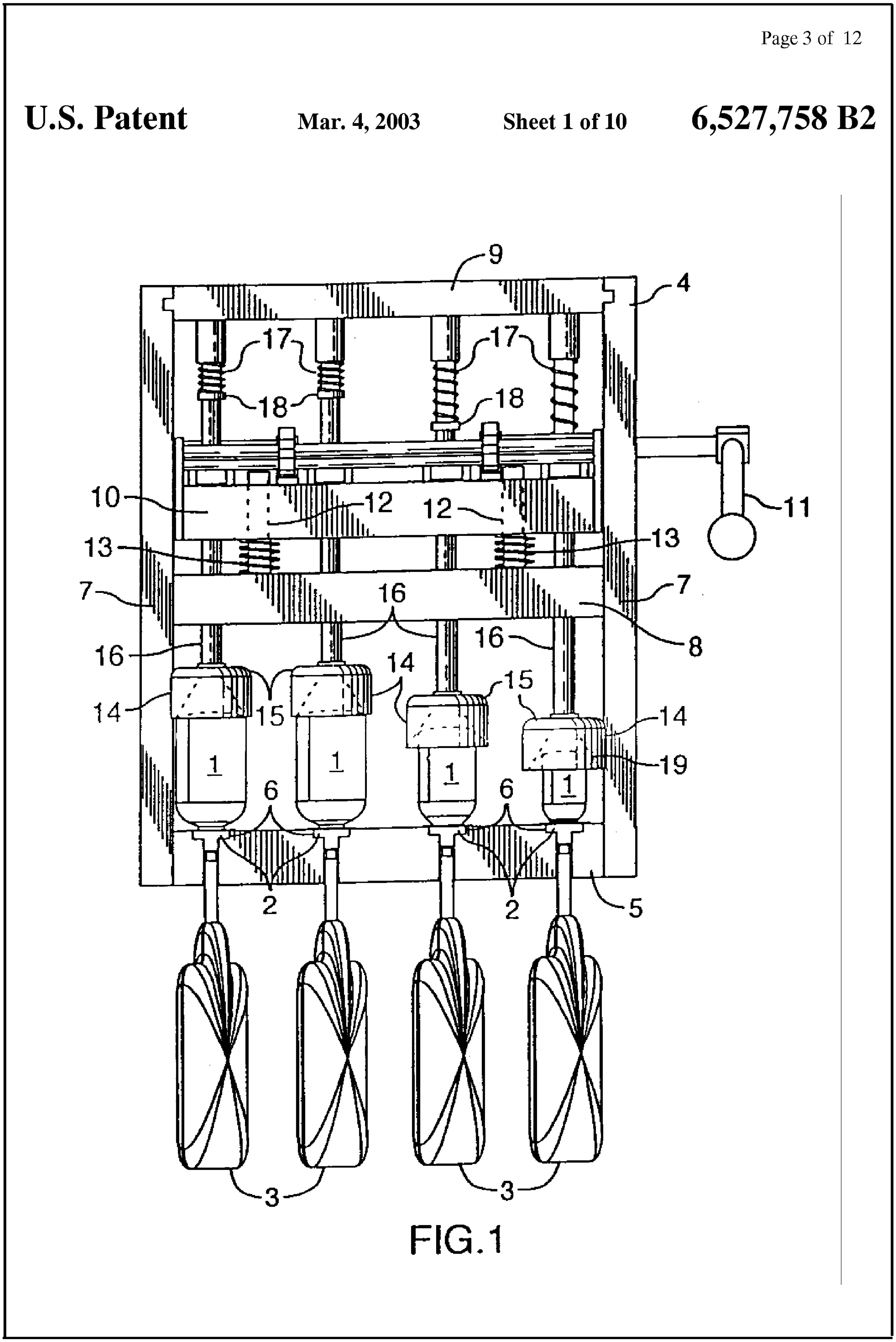
Figure 2:
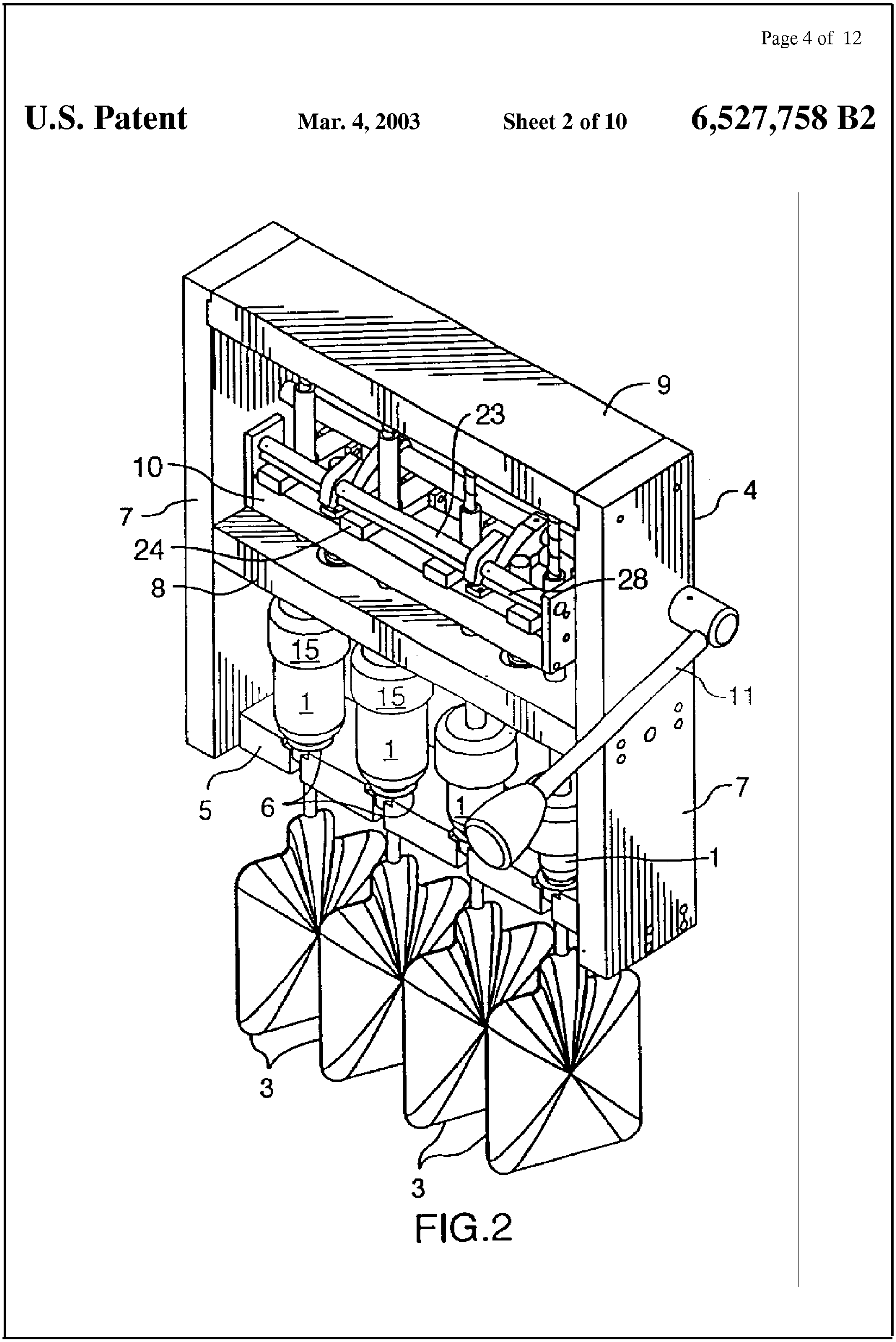
Figure 3:
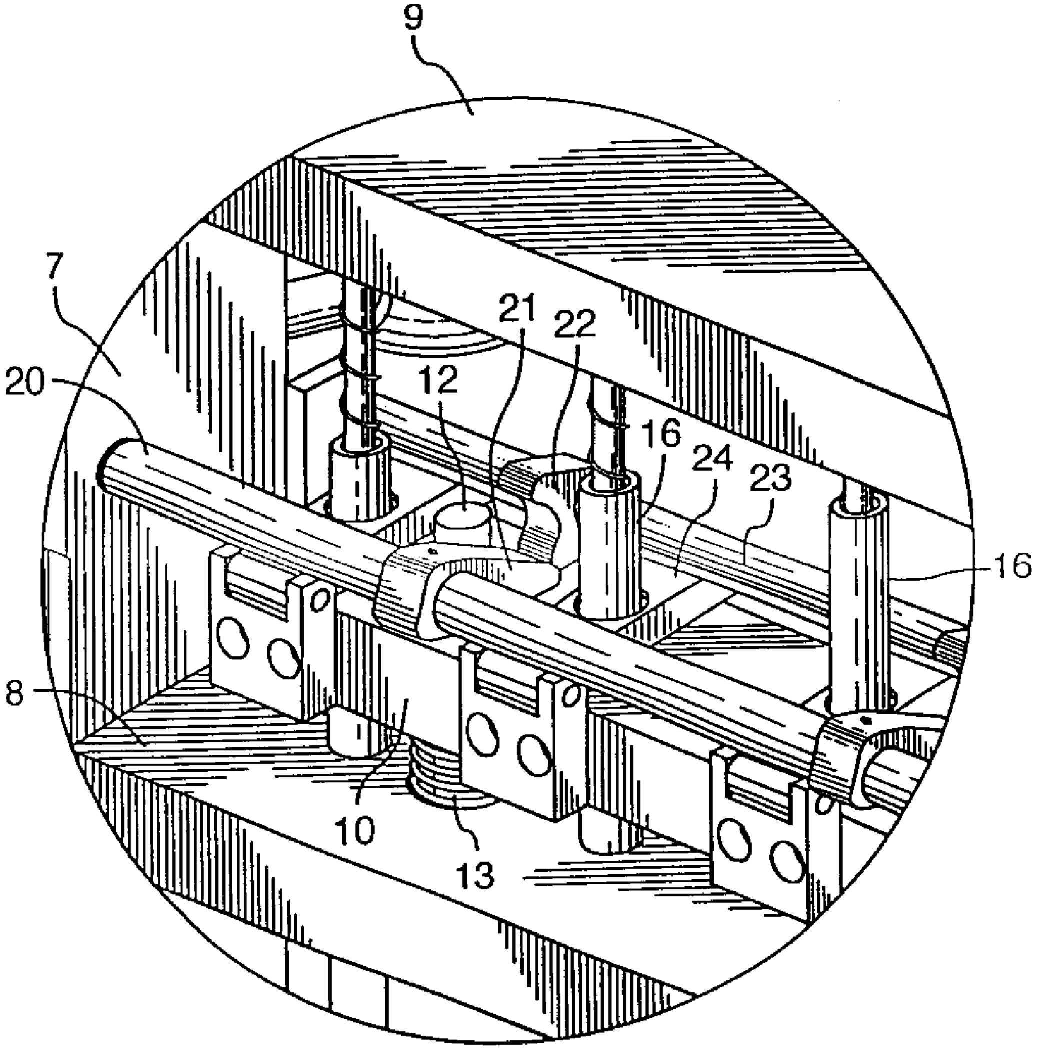
Figure 5:
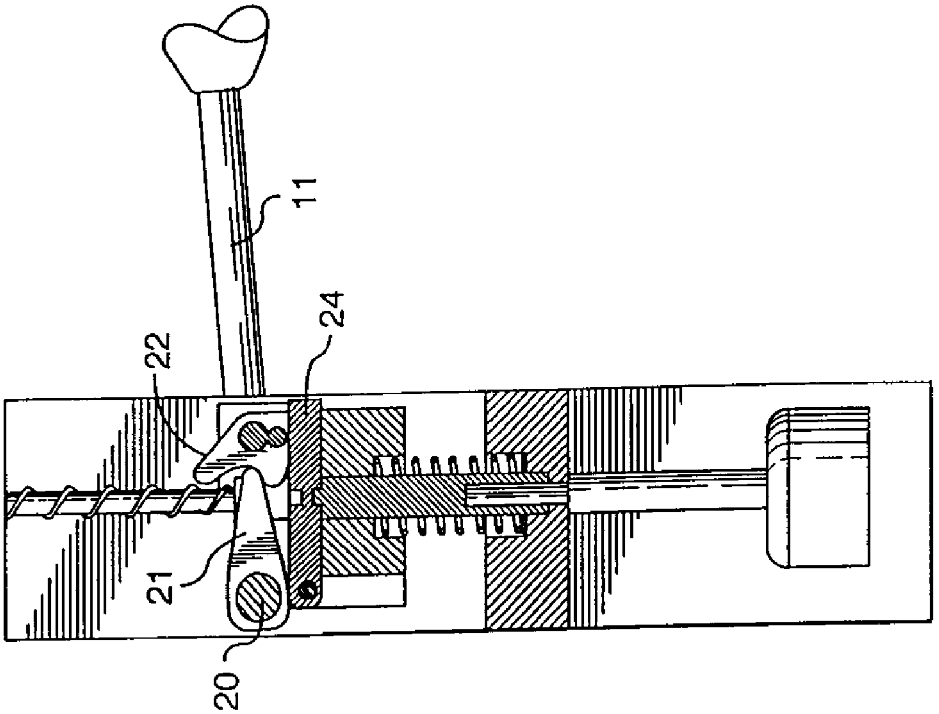
Figure 4:
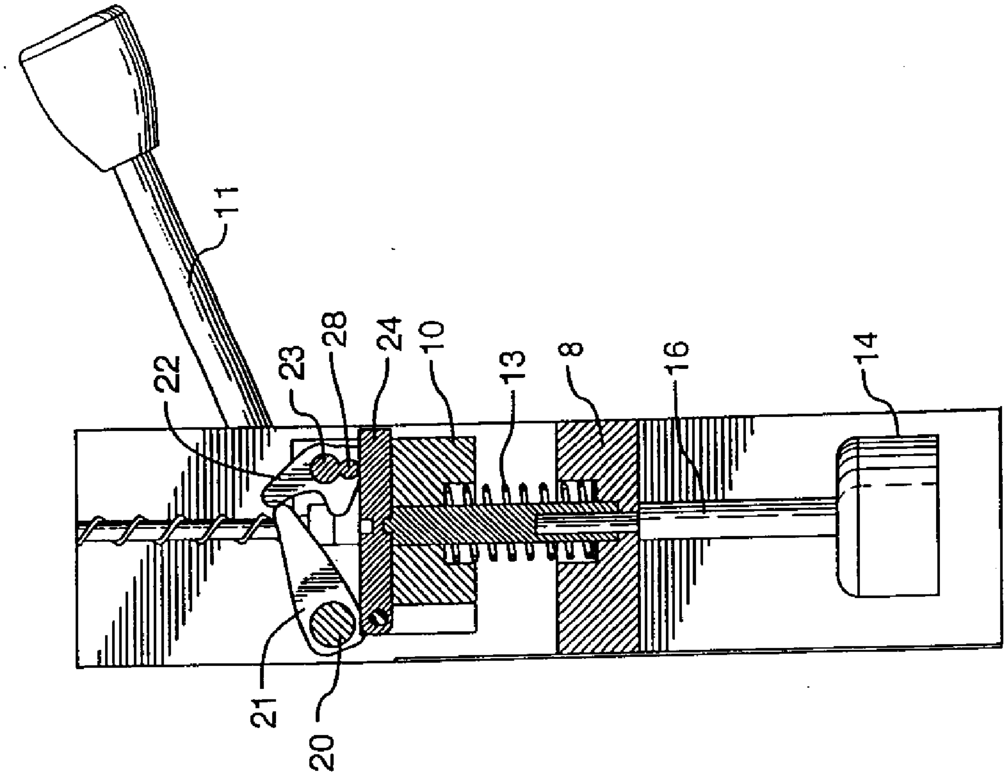
Figure 7:
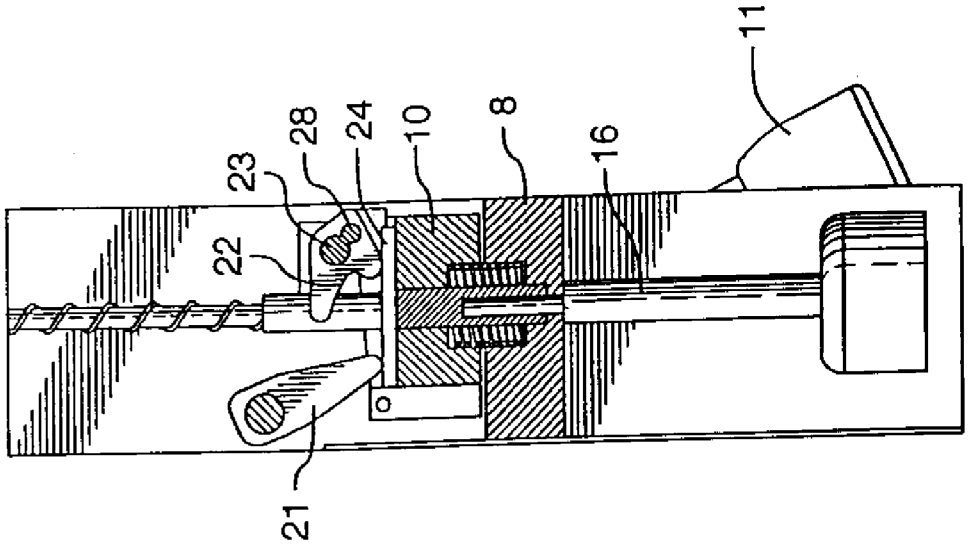
Figure 6:
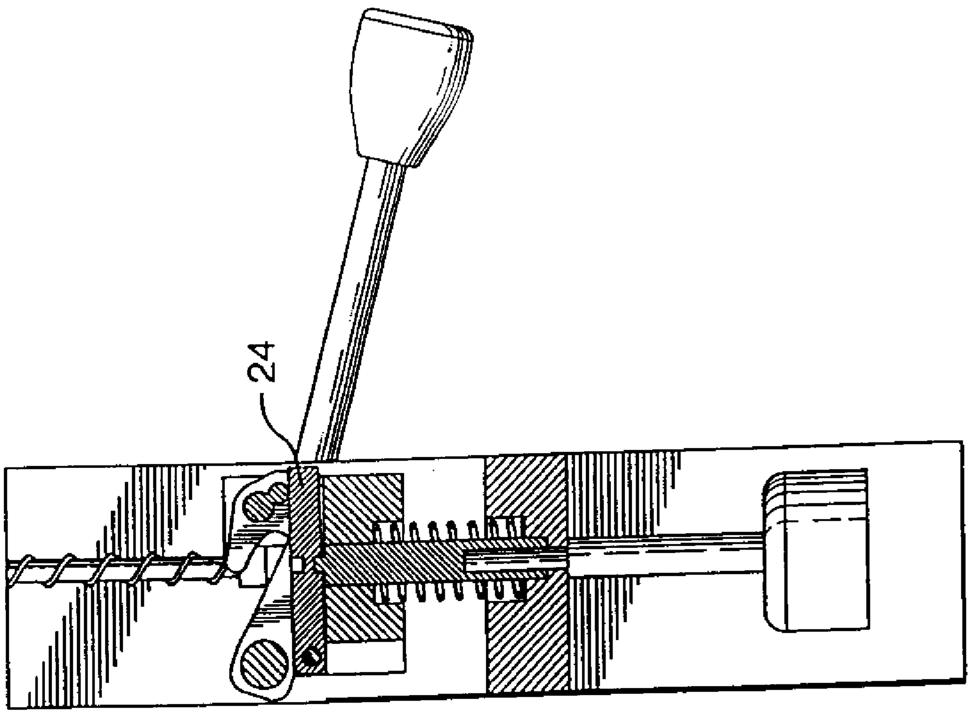
Figure 8:
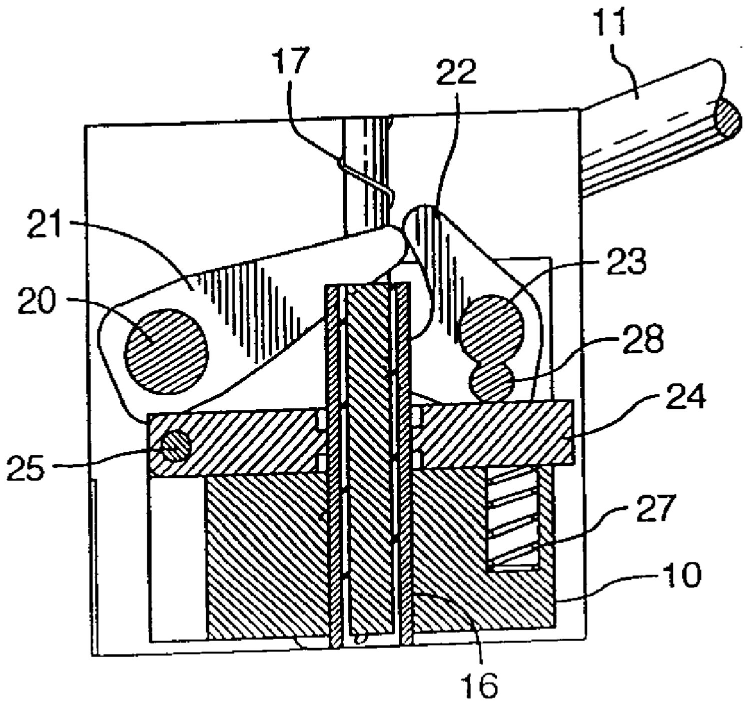
Figure 9:
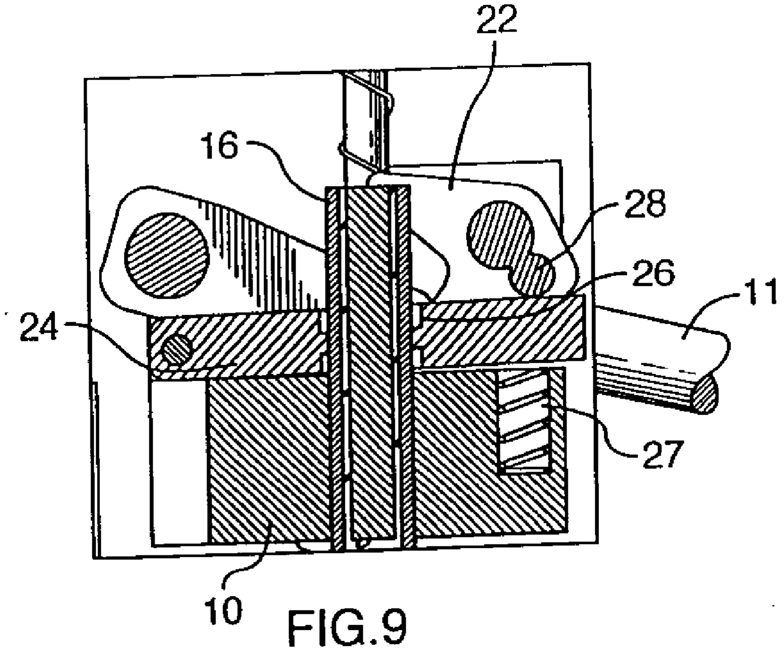
Figure 10:
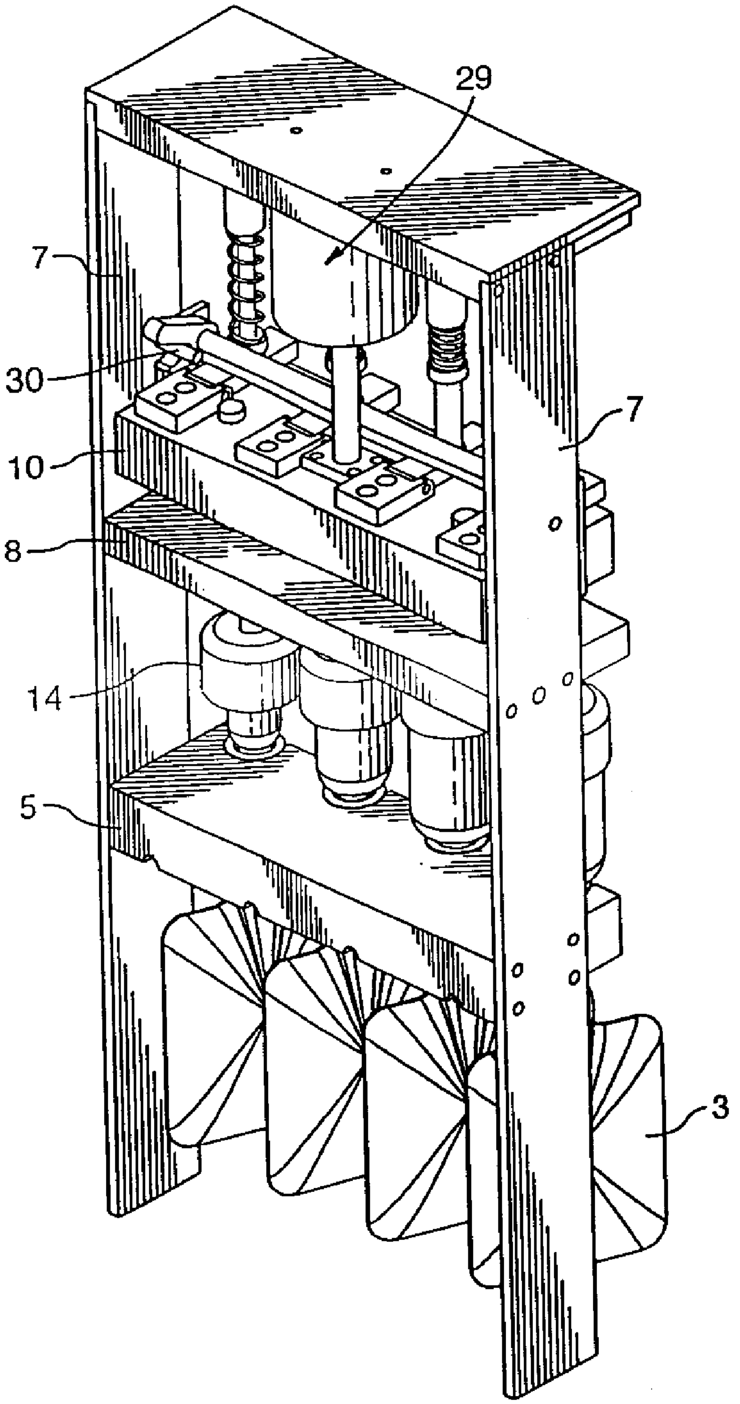
Figure 11:
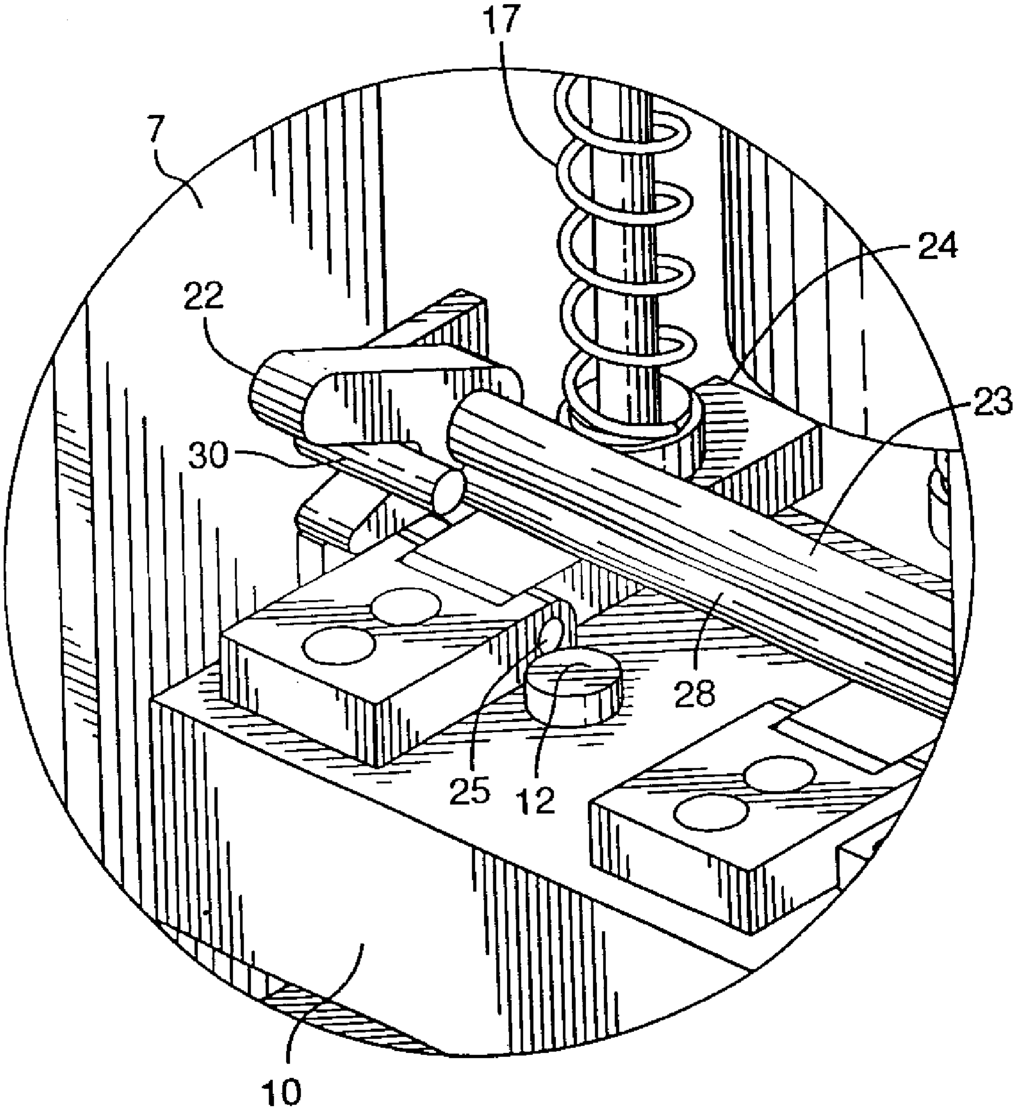
Figure 12:
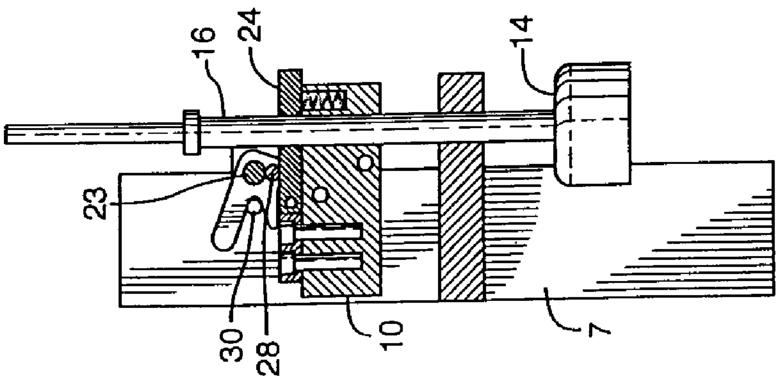
Figure 13:
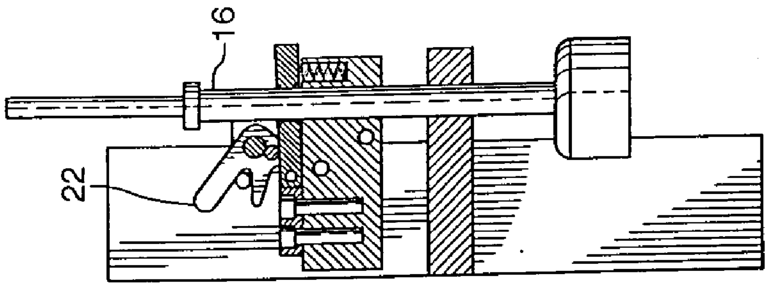
Figure 14:
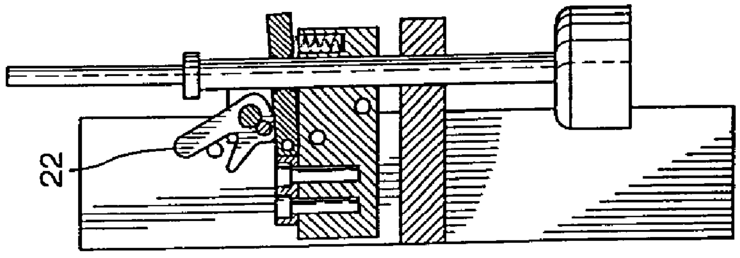
Figure 15:
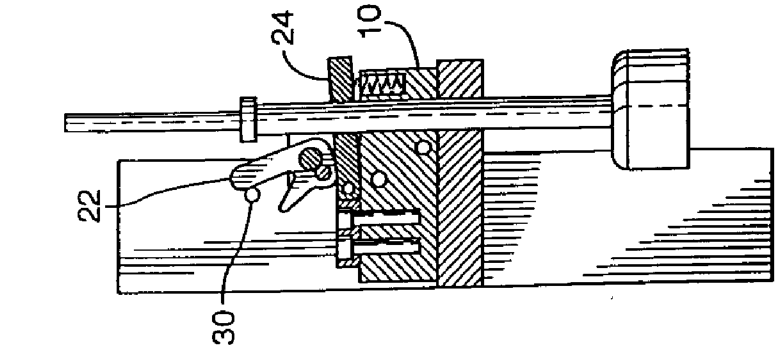
Figure 16:
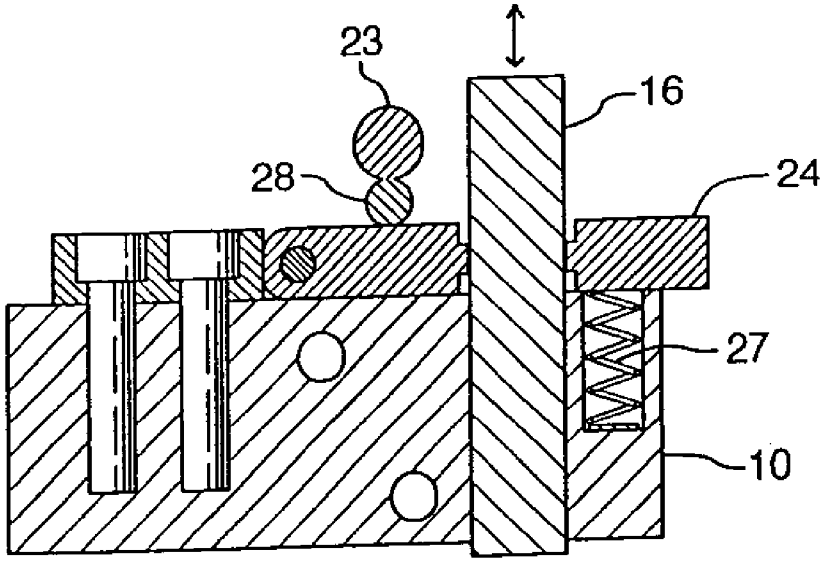
Figure 17:
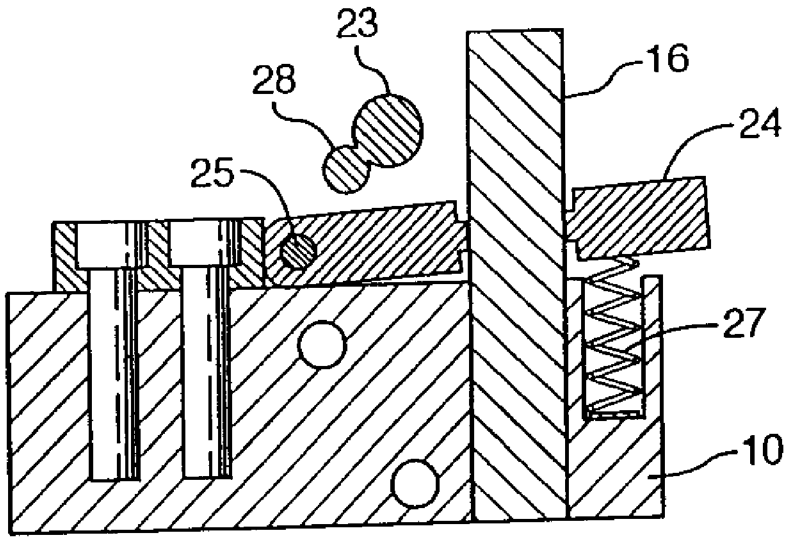

FIGS. 12, 13,14, and 15 show the progressive motion of the plunger 14 as the plunger rod 16 is clamped with lock lever 24 through the action of rotating cam shaft 23 thereby releasing engagement between the cam lobe 28 and lock lever 24, in a manner similar to that described above. FIGS. 16 and 17 show means by which the rods 16 and lock levers 24 are engaged and disengaged under the action of spring 27 as the lock lever 24 rotates about pin 25.

Figure 11:
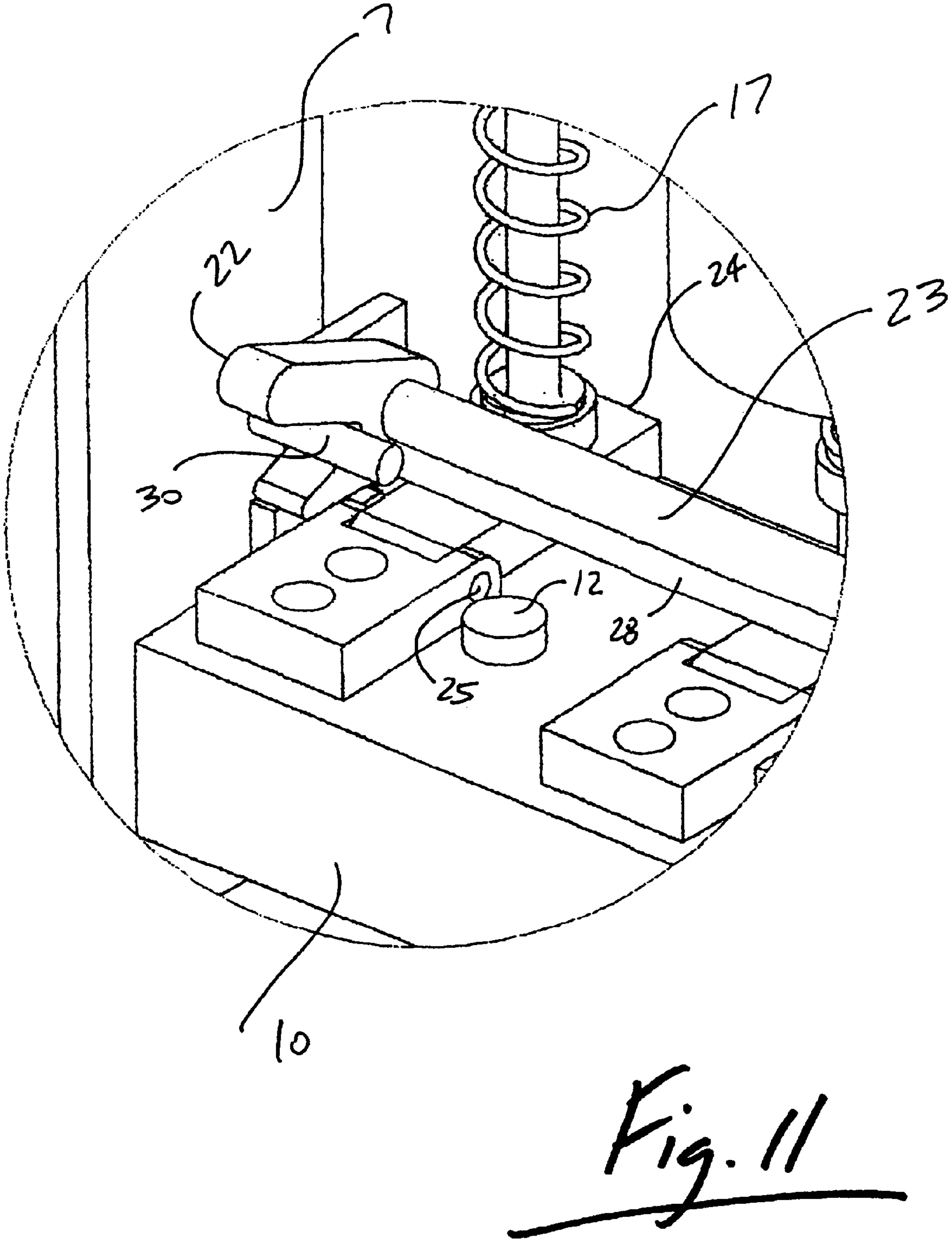
FIG. 11 shows a detailed view of the end cam followers engaging a pin mounted to the frame for rotating the cam shaft as the cam shaft and header beam move downwardly thereby releasing the spring loaded lock levers to bind on the rods of the plunger.
Figures 12, 13, 14, 15:
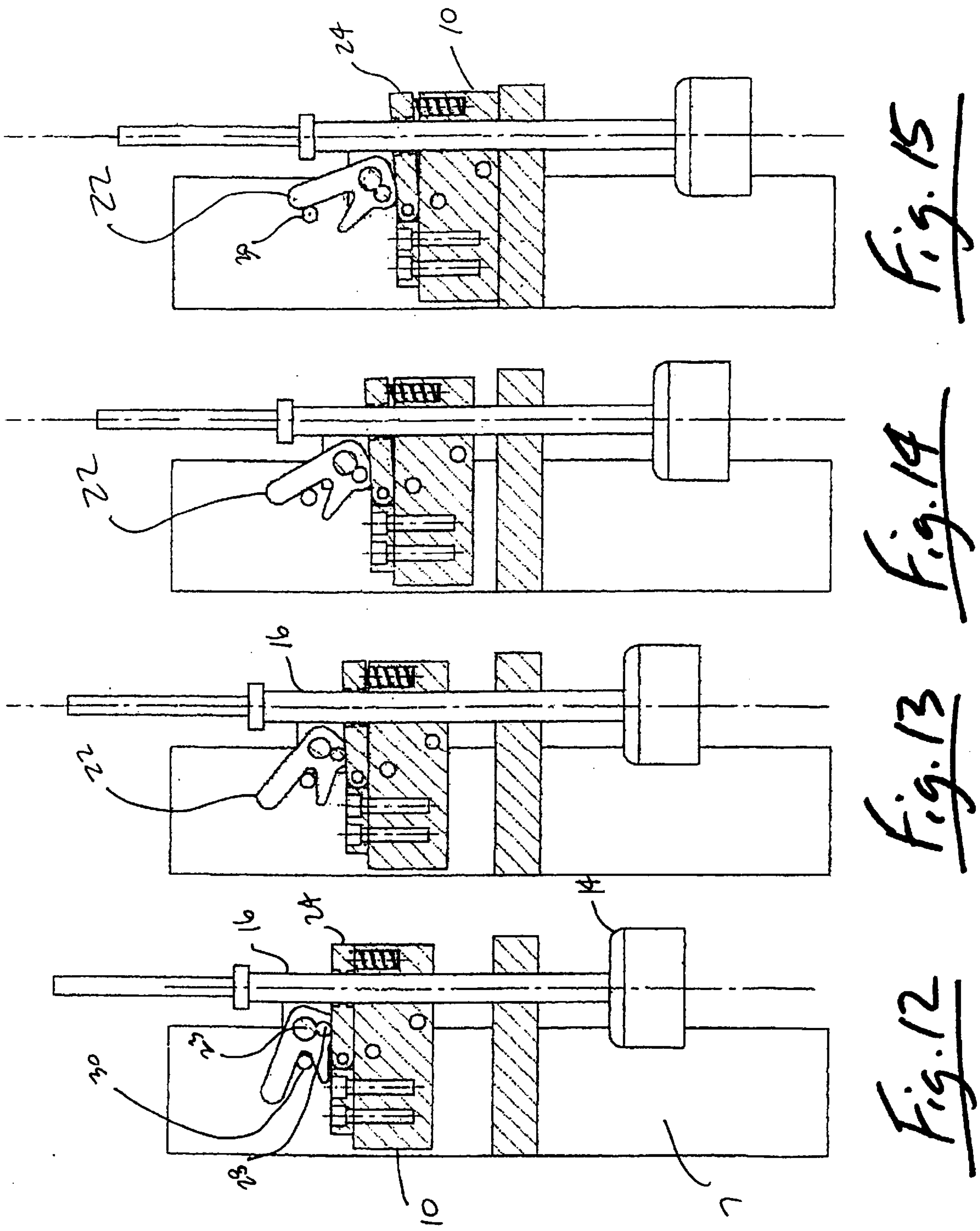
FIGS. 12, 13, 14 and 15 show the progressive rotation of the cam shaft with cam follower engaging the pin projecting from the frame side wall and showing the releasing of the lock levers spring loaded to a position which binds at an angle to the rod of the plunger.

However, as seen in the detail of FIG. 11 as well as FIGS. 12 through 15, the rotation of the cam shaft 23 is performed in a different manner. The up and down motion of the header block 10 is controlled by the stroke of the cylinder 29. Due to the possibility of physical injury to operators using an automated device, it is likely necessary to ensure that both of the operator's hands are out of the way of the plungers 14 and header block 10 before the cylinder 29 is activated. Therefore conventional twin push buttons are recommended for safety reasons.

The progression shown in FIGS. 12 through 15 and detail of the end view of the cam shaft 23 in FIG. 11 indicate that each of the frame side walls 7 include a pin 30. In the mechanical operated embodiment, the cam follower 22 mounted to the cam shaft 23 is located at the two ends of the cam shaft 23 and has a different profile to interact with the pin 30 projecting from the frame side wall 7. As shown in the progression through FIGS. 12, 13, 14 and 15, the interaction between the moving cam surface of cam follower 22 with the stationary pin 30 results in a simple mechanism which rotates the cam shaft 23 and thereby engages and disengages the cam lobe 28 from the top surface of each lock lever 24.

As described above, the invention includes both a manually operated version in FIGS. 1–9 and a mechanically operated version in FIGS. 10–17, both of which utilize many common features such as plungers 14, movable header block 10 and lock levers 24. The invention overcomes the disadvantages of the prior art in enabling simple accommodation of various different sizes of vials simultaneously as shown in FIG. 1 with a simple mechanism that is inexpensive and easy to operate.

Although the above description relates to a specific preferred embodiment as presently contemplated by the inventor, it will be understood that the invention in its broad aspect includes mechanical and functional equivalents of the elements described herein.

I claim:

1. A vial docking station for simultaneously sliding the spouts of a plurality of same or different sized vials into an engaged position with matching receptacles of a like plurality of diluent bags, the vial docking station comprising:

a frame including a bag mounting block with a plurality of spaced apart receptacle mounts;

a header block mounted to the frame with a like plurality of plungers, each plunger biased to engage a base of an associated vial in a ready position wherein the vial spout is aligned with an associated receptacle, each plunger being manually individually operable between the ready position and a retracted position wherein the vial base is disengaged from the plunger;

plunger clamping means, comprising a plurality of plunger clamps disposed on the header block, for releasably clamping each plunger to inhibit relative motion between the plunger and the header block; and stroke means, comprising an actuation mechanism mounted to the frame, engaging the plunger clamps and at least one of the header block and the bag mounting block, for moving the header block and bag mounting block progressively from the ready position forward to the engaged position, and rearward to a withdrawn position and for actuating the plunger clamps to during movement between the ready position and the withdrawn position.

2. A vial docking station according to claim 1 wherein the plungers comprise: a head with a vial base mating socket; and a rod slidably mounted to the header block.

3. A vial docking station according to claim 2 wherein the plunger head is spring loaded toward the bag mounting block.

4. A vial docking station according to claim 2 wherein the plunger head includes a conical self-centering vial base mating socket.

5. A vial docking station according to claim 2 wherein the plunger clamp comprises: a lock lever pivotally mounted to the header block for rotation about an axis transverse to the plunger rod, the rod extending through an aperture through the lock lever, the lock lever moving between a free sliding position and a clamped position wherein lock lever is disposed relative to the plunger rod with peripheral edges of the aperture gripping an outer surface of the rod.

6. A vial docking station according to claim 5 wherein the actuation mechanism comprises a cam shaft rotatably mounted to the header block having a clamp cam lobe fixed thereon engaging said lock levers.

7. A vial docking station according to claim 5 wherein the cam shaft includes cam follower means engaging the frame for rotating the cam shaft as the header block progresses between the ready position, the engaged position and the withdrawn position.

8. A vial docking station according to claim 1 wherein the actuation mechanism is manually operable comprising: biasing means between the header and bag mounting blocks for biasing the header and bag mounting blocks apart; and a crank shaft rotatably mounted to the header block with a crank arm extending transversely from at least one end thereof, the crank shaft including at least one lever arm extending transversely from the crank shaft and engaging the header block.

9. A vial docking station according to claim 8 wherein:

the plunger clamp comprises: a lock lever pivotally mounted to the header block for rotation about an axis transverse to the plunger rod, the rod extending through an aperture through the lock lever, the lock lever moving between a free sliding position and a clamped position wherein lock lever is disposed relative to the plunger rod with peripheral edges of the aperture gripping an outer surface of the rod;

the actuation mechanism comprises a cam shaft rotatably mounted to the header block having a clamp cam lobe fixed thereon engaging said lock levers, the cam shaft including cam follower means engaging the lever arm of the crank shaft for rotating the cam shaft as the crank shaft rotates.

10. A vial docking station according to claim 1, wherein the actuation mechanism is selected from the group consisting of: slide mountings between the header block and frame; slide mountings between the bag mounting block and the frame; a manually operable mechanism; a pneumatic actuator; and a hydraulic actuator.

* * * * *

UNITED STATES PATENT AND TRADEMARK OFFICE

CERTIFICATE OF CORRECTION

PATENT NO. : 6,527,758 B2
DATED : March 4, 2003
INVENTOR(S) : Ko

It is certified that error appears in the above-identified patent and that said Letters Patent is hereby corrected as shown below:

Title page illustrating a drawing figure should be deleted, and substitute therefor a title page illustrating a figure as shown on the attached sheet.

Delete drawing sheets 1-10, and substitute therefore drawing sheets 1-10. (Attached)

Signed and Sealed this

Twenty-first Day of December, 2004

JON W. DUDAS
*Director of the United States Patent and Trademark Office*

(12) United States Patent
Ko

(10) Patent No.: US 6,527,758 B2
(45) Date of Patent: Mar. 4, 2003

(54) VIAL DOCKING STATION FOR SLIDING RECONSTITUTION WITH DILUENT CONTAINER

(76) Inventor: Kam Ko, 92 Morrison Crescent, Unionville, Ontario (CA), L3R 9K8

(*) Notice: Subject to any disclaimer, the term of this patent is extended or adjusted under 35 U.S.C. 154(b) by 0 days.

(21) Appl. No.: 09/878,543

(22) Filed: Jun. 11, 2001

(65) Prior Publication Data

US 2002/0188273 A1 Dec. 12, 2002

(51) Int. Cl.$^{7}$ .......................... A61B 19/00; A61B 17/43

(52) U.S. Cl. ....................... 604/403; 604/410; 604/411; 604/412; 604/414; 604/415; 604/416; 604/905

(58) Field of Search ................................ 604/403, 410, 604/411, 412, 414, 415, 416, 83, 88, 905; 222/81; 137/614.04; 206/221, 265

(56) References Cited

U.S. PATENT DOCUMENTS 1,657,782 A 1/1928 Berg
3,245,586 A 4/1966 Haggitt .......................... 222/88
RE30,610 E 5/1981 Gacki et al. ............... 366/153
4,936,841 A 6/1990 Aoki et al. ................ 604/413
5,037,390 A 8/1991 Raines et al. ............... 604/83
5,190,525 A * 3/1993 Oswald et al. ............... 604/83
5,329,976 A * 7/1994 Haber et al. ................. 141/18
5,364,386 A 11/1994 Fukuoka et al. ........... 604/411
5,372,593 A * 12/1994 Boehringer et al. ........ 604/317
5,409,141 A 4/1995 Kikuchi et al. .............. 222/81
5,478,337 A 12/1995 Okamoto et al. .......... 604/413
5,596,193 A * 1/1997 Chutjian et al. ........... 250/281
5,782,382 A * 7/1998 Van Marcke .............. 222/105
5,826,713 A 10/1998 Sunago et al. ............. 206/222
6,063,068 A * 5/2000 Fowles et al. ............. 604/411
6,065,649 A 5/2000 Scoggins ................. 222/181.2
6,070,761 A 6/2000 Bloom et al. ................ 222/81
6,113,583 A 9/2000 Fowles et al. ............. 604/403

* cited by examiner

*Primary Examiner*—William C. Doerrler
*Assistant Examiner*—Filip Zec
(74) *Attorney, Agent, or Firm*—Mark Kusner; Michael A. Jaffe

(57) ABSTRACT

A vial docking station for simultaneously sliding the spouts of a plurality of liquid medicament vials into an engaged position with matching receptacles of a like plurality of liquid reconstitution diluent bags.

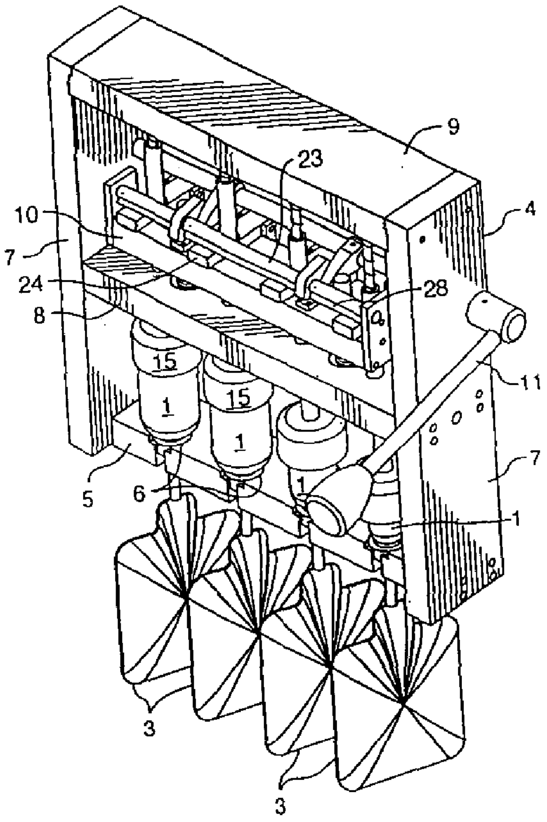

10 Claims, 10 Drawing Sheets